United States Patent
Hayashi et al.

(10) Patent No.: US 8,148,427 B2
(45) Date of Patent: Apr. 3, 2012

(54) BENZYLAMINE DERIVATIVE OR PHARMACEUTICALLY ACCEPTABLE ACID ADDITION SALT THEREOF, AND USE THEREOF FOR MEDICAL PURPOSES

(75) Inventors: Ryoji Hayashi, Kanagawa (JP); Tsukasa Kikuchi, Kanagawa (JP); Masaki Arai, Kanagawa (JP); Satoshi Kurosawa, Kanagawa (JP); Ko Hasebe, Kanagawa (JP); Sayoko Kanie, Kanagawa (JP); Seiichiro Ozono, Shizuoka (JP); Atsushi Otsuka, Shizuoka (JP)

(73) Assignee: Toray Industries, Inc. (JP)

( * ) Notice: Subject to any disclaimer, the term of this patent is extended or adjusted under 35 U.S.C. 154(b) by 301 days.

(21) Appl. No.: 12/525,364

(22) PCT Filed: Jan. 31, 2008

(86) PCT No.: PCT/JP2008/051479
§ 371 (c)(1),
(2), (4) Date: Jul. 31, 2009

(87) PCT Pub. No.: WO2008/093767
PCT Pub. Date: Aug. 7, 2008

(65) Prior Publication Data
US 2010/0099769 A1    Apr. 22, 2010

(30) Foreign Application Priority Data
Jan. 31, 2007    (JP) ................................. 2007-020582

(51) Int. Cl.
*A61K 31/18* (2006.01)
*C07C 307/00* (2006.01)
*A61P 13/00* (2006.01)

(52) U.S. Cl. .......................................... 514/605; 564/99
(58) Field of Classification Search .................. 514/605; 564/99
See application file for complete search history.

(56) References Cited

U.S. PATENT DOCUMENTS

| 3,341,584 | A | 9/1967 | Larsen et al. |
| 6,346,532 | B1 | 2/2002 | Maruyama et al. |
| 6,495,546 | B1 | 12/2002 | Taniguchi et al. |
| 2002/0068751 | A1 | 6/2002 | Coghlan et al. |
| 2004/0167167 | A1 | 8/2004 | Mammen et al. |

FOREIGN PATENT DOCUMENTS

| EP | 0 659 737 A2 | 6/1995 |
| EP | 1 174 426 A1 | 1/2002 |
| JP | 07-206806 | 8/1995 |

OTHER PUBLICATIONS

Sum, F-W et al., "Cyclic Amine Sulfonamides as Linkers in the Design and Synthesis of Novel Human $\beta_3$ Adrenergic Receptor Agnostics," *Bioorganic & Medicinal Chemistry Letters*, 2003, vol. 13, pp. 2191-2194.

Wheeldon et al., "Cardiac Effects of the $\beta$3-adrenoceptor Agonist BRL35135 in Man", 1994, vol. 37, pp. 363-369, *Department of Clinical Pharmacology, Ninewells Hospital and Medical School*, Dundee DDI9SY, Scotland.

Washburn et al., "Beta 3 Agonusts, Part 1; Evolution from Inception to BMS-19449*1", 2001, vol. 2, Issue 23, pp. 3035-3039 *Bioorganic & Medicinal Chemistry Letters*.

*Primary Examiner* — Sreeni Padmanabhan
*Assistant Examiner* — Sahar Javanmard
(74) *Attorney, Agent, or Firm* — DLA Piper LLP (US)

(57) ABSTRACT

The benzylamine derivative represented by the formula below and a pharmaceutically acceptable acid addition salt thereof, and a pharmaceutical containing the derivative or the pharmaceutically acceptable acid addition salt thereof, and a therapeutic or prophylactic agent for pollakiuria or urinary incontinence containing the derivative or the pharmaceutically acceptable acid addition salt thereof are provided. The benzylamine derivative of the present invention and the pharmaceutically acceptable acid addition salt thereof have less possibility of occurrence of side effects than known compounds, and show a better therapeutic effect against pollakiuria or urinary incontinence, so that they can be used as excellent therapeutic or prophylactic agents for pollakiuria or urinary incontinence.

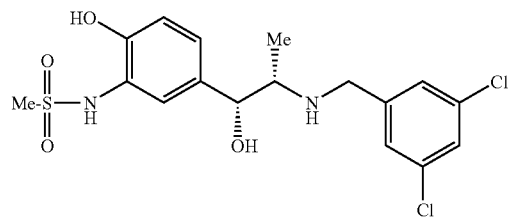

11 Claims, No Drawings

BENZYLAMINE DERIVATIVE OR PHARMACEUTICALLY ACCEPTABLE ACID ADDITION SALT THEREOF, AND USE THEREOF FOR MEDICAL PURPOSES

RELATED APPLICATIONS

This is a §371 of International Application No. PCT/JP2008/051479, with an international filing date of Jan. 31, 2008 (WO 2008/093767 A1, published Aug. 7, 2008), which is based on Japanese Patent Application No. 2007-020582, filed Jan. 31, 2007.

TECHNICAL FIELD

This disclosure relates to a novel benzylamine derivative or a pharmaceutically acceptable acid addition salt thereof, a pharmaceutical comprising the same, and a therapeutic or prophylactic agent comprising the same for pollakiuria or urinary incontinence.

BACKGROUND

With the growth of the aged population in recent years, the number of patients suffering from pollakiuria or urinary incontinence is increasing. At present, as therapeutic agents for pollakiuria or urinary incontinence, agents having anticholinergic activities and/or muscle relaxant activities are mainly used. However, administration of these therapeutic agents are associated with side effects, for example, dry mouth; gastrointestinal system symptoms such as constipation; cardiovascular symptoms such as orthostatic hypotension; or urinary dysfunction such as urinary retention and residual urine, so that they may not be able necessarily to be administered up to the dose in which their effectiveness is shown. For improvement of quality of life (QOL) of patients, development of a therapeutic or prophylactic agent for pollakiuria or urinary incontinence with less those side effects is strongly demanded.

At present, as therapeutic or prophylactic agents for pollakiuria or urinary incontinence with less possibility of occurrence of dry mouth which is the major side effect of the existing drugs, β3 agonists have been researched and developed. However, it has been suggested that in human, a certain type of β3 agonists shows effects on cardiovascular system such as increase in heart rate and increase in cardiac output, and has a positive chronotropic effect on the heart (Br. J. Clin. Pharmac. 37, 363, 1994). For a therapeutic agent for pollakiuria or urinary incontinence, effects on cardiovascular system are side effects, and in cases where they are severe, they may be factors due to which therapy is stopped, so that a therapeutic agent for pollakiuria or urinary incontinence, from which effects on cardiovascular system are separated to the greatest extent possible, is demanded.

In Japanese Translated PCT Patent Application Laid-open No. 2002-512639, a compound useful for therapy of pollakiuria as a β3 agonist is disclosed, and more particularly, the phenethylamine derivative 1 is disclosed as a therapeutic agent for urinary dysfunction:

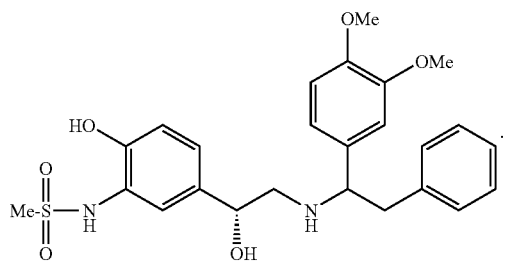

However, this prior art reference does not suggest at all that the compound herein, whose structural requirements are different from those of the compound included in the prior art reference, has an anti-pollakiuria activity at a dose at which there is only a very small possibility of occurrence of side effects on cardiovascular system (especially, the heart rate-increasing effect and hypotensive effect), and that the compound is especially useful as a therapeutic or prophylactic agent for pollakiuria or urinary incontinence.

On the other hand, in Bioorg. Med. Chem. Lett., 2001, 11, 3035, the benzylamine derivative 2, which is structurally similar to the compounds herein, and its affinity, selectivity and agonistic activity to β3 receptor are disclosed:

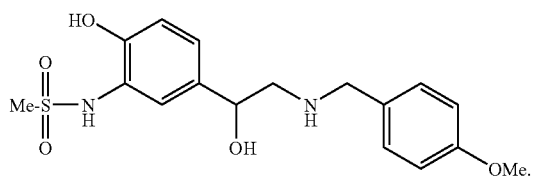

However, its effects as a therapeutic or prophylactic agent for pollakiuria or urinary incontinence, and side effects on cardiovascular system are not disclosed at all.

In U.S. Pat. No. 3,341,584 B, a wide range of compounds including a part of the compounds herein are disclosed. However, the literature is totally silent about effects of these compounds as therapeutic or prophylactic agents for pollakiuria or urinary incontinence. Further, in the literature, compounds having a benzylamine structure characteristic to the compounds herein are not concretely described.

Thus, it could be helpful to provide a novel compound useful as an excellent therapeutic or prophylactic agent for pollakiuria or urinary incontinence with only a very small possibility of occurrence of side effects on cardiovascular system, a pharmaceutical comprising the compound, and a therapeutic or prophylactic agent comprising the compound for pollakiuria or urinary incontinence.

SUMMARY

We intensively studied to discover novel benzylamine derivatives which are excellent in the selectivity on β3 receptor, and discovered that they have an excellent effect on therapy or prophylaxis of pollakiuria or urinary incontinence and that there is only a very small possibility of occurrence of side effects on cardiovascular system (the heart rate-increasing effect and hypotensive effect).

We thus provide a benzylamine derivative represented by the General Formula (I):

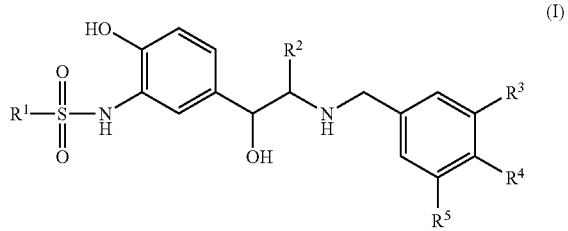

[wherein $R^1$ is $C_1$-$C_6$ alkyl, $R^2$ is $C_1$-$C_6$ alkyl, $R^3$ and $R^5$ are each independently $C_1$-$C_6$ alkyl, $C_1$-$C_6$ haloalkyl, $C_1$-$C_6$ alkoxy or halogen, and $R^4$ is hydrogen or $C_1$-$C_6$ alkoxy] or a pharmaceutically acceptable acid addition salt thereof; and a pharmaceutical comprising the derivative or the pharmaceutically acceptable acid addition salt thereof; and a therapeutic or prophylactic agent comprising the derivative or the pharmaceutically acceptable acid addition salt thereof for pollakiuria or urinary incontinence. Further, we provide a method for therapy or prophylaxis of pollakiuria or urinary incontinence, comprising administering an effective amount of the above-described benzylamine derivative of the present invention or the pharmaceutically acceptable acid addition salt thereof. Still further, we provide use of the above-described benzylamine derivative or the pharmaceutically acceptable acid addition salt thereof for the production of a pharmaceutical for treating or preventing pollakiuria or urinary incontinence. Yet further, we provide the above-described benzylamine derivative or the pharmaceutically acceptable acid addition salt thereof for treating or preventing pollakiuria or urinary incontinence.

DETAILED DESCRIPTION

The benzylamine derivative represented by the General Formula (I) or the pharmaceutically acceptable acid addition salt thereof has an excellent effect on therapy or prophylaxis of pollakiuria or urinary incontinence at a dose at which there is only a very small possibility of occurrence of side effects on cardiovascular system (the heart rate-increasing effect and hypotensive effect).

The terms below are defined as follows unless otherwise specified.

"Alkyl" means a monovalent, linear or branched, and saturated hydrocarbon group consisting of a carbon atom(s) and hydrogen atoms.

"Alkoxy" means an —OR group, wherein R is alkyl as defined herein.

"Halogen" means fluoro, chloro, bromo or iodo.

"Haloalkyl" means alkyl as defined herein, which is substituted with one or more halogens as defined herein at an arbitrary position(s).

In the benzylamine derivatives represented by the General Formula (I), examples of the $C_1$-$C_6$ alkyl for $R^1$, $R^2$, $R^3$ and $R^5$ include, but are not limited to, methyl, ethyl, propyl, isopropyl, butyl, sec-butyl, tert-butyl, pentyl and hexyl.

Examples of the $C_1$-$C_6$ haloalkyl for $R^3$ and $R^5$ include, but are not limited to, fluoromethyl, chloromethyl, difluoromethyl, dichloromethyl, trifluoromethyl, trichloromethyl, 2,2,2-trifluoroethyl and 2,2,2-trichloroethyl.

Examples of the $C_1$-$C_6$ alkoxy for $R^3$, $R^4$ and $R^5$ include, but are not limited to, methoxy, ethoxy, propoxy, isopropoxy, butoxy and tert-butoxy.

Examples of the halogen for $R^3$ and $R^5$ include, but are not limited to, fluoro, chloro, bromo and iodo.

Preferred examples of $R^1$ to $R^5$ are shown below. However, these are nothing more than specific examples, and $R^1$ to $R^5$ are not restricted thereto.

$R^1$ is preferably methyl, ethyl, propyl, isopropyl or tert-butyl, more preferably methyl or isopropyl, especially preferably methyl.

$R^2$ is preferably methyl, ethyl, propyl or isopropyl, more preferably methyl, ethyl or propyl, especially preferably methyl.

$R^3$ and $R^5$ are each independently preferably methyl, ethyl, fluoromethyl, difluoromethyl, trifluoromethyl, methoxy, ethoxy or chloro, more preferably methyl, trifluoromethyl, methoxy or chloro, and $R^3$ and $R^5$ are especially preferably simultaneously methyl, trifluoromethyl, methoxy or chloro.

$R^4$ is preferably hydrogen, methoxy, ethoxy, propoxy or isopropoxy, more preferably hydrogen, methoxy or ethoxy, especially preferably hydrogen or methoxy.

The benzylamine derivative of the General Formula (I) has two asymmetrical carbon atoms, so that optical isomers and diastereomers which are based thereon exist. The benzylamine derivative also includes these single isomers, or a racemate or diastereomer mixture thereof.

Examples of the pharmaceutically acceptable acid addition salt of the benzylamine derivative of the General Formula (I) include, but are not limited to, inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt or methanesulfonic acid salt is preferably used, and hydrochloric acid salt, tartaric acid salt or methanesulfonic acid salt is more preferably used, but the acid addition salt is not restricted thereto.

Among the benzylamine derivatives of the General Formula (I), preferred examples are shown in Table 1, but the benzylamine derivatives are not restricted by these.

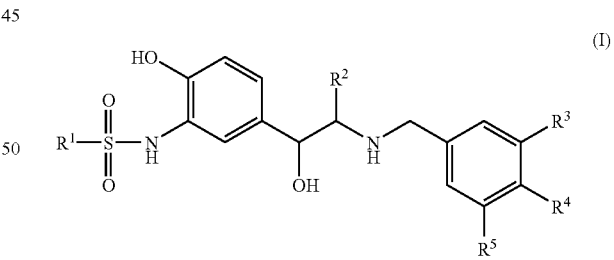

TABLE 1

| $R^1$ | $R^2$ | $R^3$ | $R^4$ | $R^5$ |
|---|---|---|---|---|
| Me | Me | Me | H | Me |
| Me | Me | Me | H | $CF_3$ |
| Me | Me | Me | H | OMe |
| Me | Me | Me | H | Cl |
| Me | Me | Me | OMe | Me |
| Me | Me | Me | OMe | $CF_3$ |
| Me | Me | Me | OMe | OMe |
| Me | Me | Me | OMe | Cl |

TABLE 1-continued

| $R^1$ | $R^2$ | $R^3$ | $R^4$ | $R^5$ |
|---|---|---|---|---|
| Me | Me | $CF_3$ | H | $CF_3$ |
| Me | Me | $CF_3$ | H | OMe |
| Me | Me | $CF_3$ | H | Cl |
| Me | Me | $CF_3$ | OMe | $CF_3$ |
| Me | Me | $CF_3$ | OMe | OMe |
| Me | Me | $CF_3$ | OMe | Cl |
| Me | Me | OMe | H | OMe |
| Me | Me | OMe | H | Cl |
| Me | Me | OMe | OMe | OMe |
| Me | Me | OMe | OMe | Cl |
| Me | Me | Cl | H | Cl |
| Me | Me | Cl | OMe | Cl |

The benzylamine derivative represented by the above-described General Formula (I) can be produced by an appropriate method based on features derived from its basic skeleton and types of its substituents. Starting materials and reagents used for production of these compounds are normally available, or can be synthesized by a method known to those skilled in the art according to a procedure described in a literature such as Organic Reaction (Wiley & Sons), Fieser and Fieser's Reagent for Organic Synthesis (Wiley & Sons).

Examples of specific production methods of the benzylamine derivatives represented by the above-described General Formula (I) include the method shown in Scheme 1:

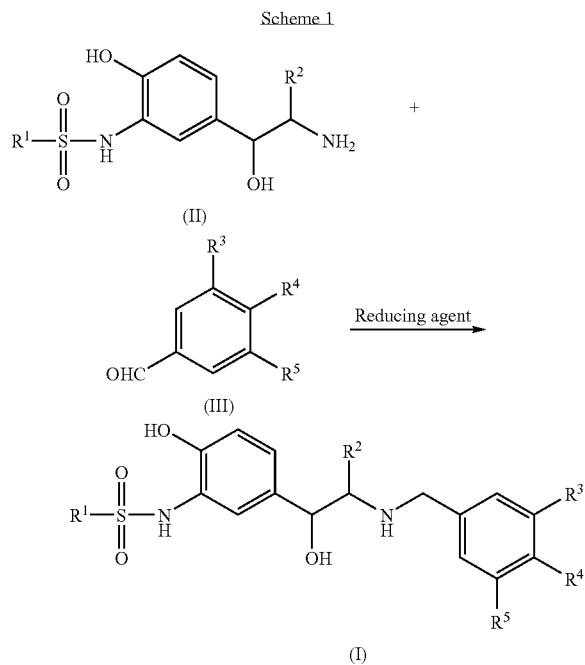

[wherein $R^1$, $R^2$, $R^3$, $R^4$ and $R^5$ represent the same meanings as described above.]

To put it concretely, the benzylamine derivative of the General Formula (I) can be obtained using a method obvious to those skilled in the art, for example, by reductive alkylation of the amine derivative represented by the General Formula (II) with the benzaldehyde derivative represented by the General Formula (III).

As the solvent, aprotic polar solvents such as dimethylformamide (DMF), dimethyl-acetamide and dimethyl sulfoxide (DMSO); ether solvents such as diethylether, tetrahydrofuran (THF), dimethoxyethane (DME) and dioxane; hydrocarbon solvents such as benzene, toluene and xylene; halogenated solvents such as dichloromethane, chloroform and 1,2-dichloroethane; alcoholic solvents such as methanol, ethanol and propanol; and mixtures thereof may be employed. Normally, preferred results are obtained when an alcoholic solvent such as methanol or ethanol, especially methanol is employed. The benzaldehyde derivative (III) may be used in an amount of 0.5 to 20 equivalents, usually 0.5 to 10 equivalents, preferably 0.5 to 3 equivalents, for the amine derivative (II).

As the reducing agent, sodium borohydride, sodium cyanoborohydride, sodium triacetoxy borohydride, borane-pyridine complex or the like may be used, and especially, sodium cyanoborohydride or borane-pyridine complex is preferably used. The reducing agent may be used in an amount of 0.5 to 50 equivalents, usually 1 to 20 equivalents, preferably 1 to 10 equivalents, for the amine derivative (II).

As for the reaction temperature, satisfactory results are obtained usually at −40° C. to 150° C., preferably −30° C. to 80° C. The reaction time is appropriately selected depending on the conditions such as the reaction temperature, and satisfactory results are usually obtained when the reaction time is about 30 minutes to 10 hours. The concentration of the substrate (II) in the reaction mixture is not restricted, and 1 mmol/L to 1 mol/L is usually preferred.

The thus obtained benzylamine derivative (I) can be made to be an acid addition salt by addition of an acid in an appropriate solvent. As the solvent, halogenated solvents such as dichloromethane, chloroform and 1,2-dichloroethane; alcoholic solvents such as methanol, ethanol and propanol; ether solvents such as dioxane and diethylether; and mixtures thereof may be employed. Normally, preferred results are obtained when an alcoholic solvent or an ether solvent, especially methanol, propanol or dioxane is employed. The amount of the acid added is not restricted, and the reaction may be carried out with the acid in an amount within the range of 1 to 30 equivalents with respect to the benzylamine derivative (I), and usually, satisfactory results are obtained with 1 to 10 equivalents, preferably 1 to 5 equivalents of the acid for the benzylamine derivative (I).

For example as shown in Scheme 2, the amine derivative represented by the General Formula (II), which is the starting material of Scheme 1, can be obtained by debenzylation which is a method obvious to those skilled in the art of the amine represented by the General Formula (IV) which can be synthesized by the method described in WO2005/040093. In general, debenzylation is carried out by hydrogenolysis in the presence of a metal catalyst:

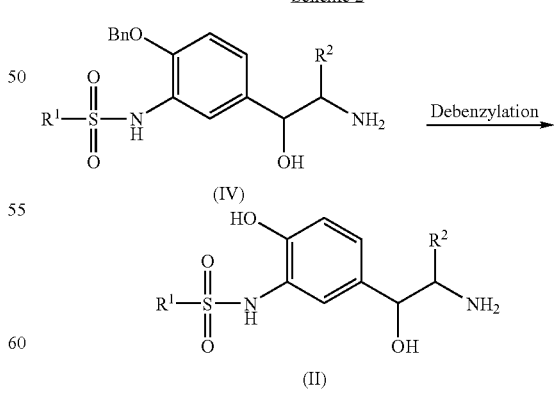

[wherein $R^1$ and $R^2$ represent the same meanings as described above, and Bn represents a benzyl group.]

As the reaction solvent, preferred results are obtained by using an alcoholic solvent such as methanol, ethanol or propanol. An ether solvent such as tetrahydrofuran (THF), dimethoxyethane (DME) or dioxane may be used as it is, and preferred results are also obtained by mixing an alcoholic solvent such as methanol or ethanol therewith. As the metal catalyst, although any catalyst used for a usual hydrogenation reaction, such as platinum oxide, palladium hydroxide or palladium-carbon, may be used, palladium hydroxide or palladium-carbon is preferably employed. The metal catalyst may be used in an amount of 0.001 to 50 equivalents, usually 0.05 to 20 equivalents, preferably 0.1 to 5 equivalents, for the amine (IV). The reaction may be carried out at a reaction temperature of −30° C. to 80° C., preferably 10° C. to 50° C., under a hydrogen pressure of 1 atm to 100 atm, preferably 1 atm to 30 atm, and preferred results are usually obtained at room temperature under normal pressure. The reaction time is appropriately selected depending on the conditions, and satisfactory results are usually obtained when the reaction time is 30 minutes to 48 hours. The concentration of the substrate (IV) in the reaction mixture is not restricted, and 1 mmol/L to 1 mol/L is usually preferred.

The effectiveness of the compound for therapy or prophylaxis of pollakiuria or urinary incontinence may be confirmed by the relaxing activity against isolated bladder smooth muscle according to the method of the literature [J. Pharmacol. Exp. Ther., 293, 939 (2000)], or by the effect of decreasing the number of voiding episodes in a given period of time in a normal rat according to the method of the literature [Jpn. J. Pharmacol., 87, 27 (2001)], but the method for confirmation of the effectiveness is not necessarily restricted thereto. The fact that the compound has only a very small possibility of occurrence of side effects on cardiovascular system may be confirmed by observing the hypotensive effect in a small animal under anesthesia, according to the method described in Experimental Methods in Pharmacology, 5th Revised Edition, KYODO ISHO SHUPPAN CO., LTD., p. 166, but the method for confirmation of the fact is not necessarily restricted thereto.

Since the compound has the relaxing activity against isolated bladder smooth muscle or the effect of decreasing the number of voiding episodes in a given period of time in a normal rat, and has only a very small possibility of occurrence of side effects on cardiovascular system (the heart rate-increasing effect and hypotensive effect), it may be used as a pharmaceutical, preferably as a therapeutic or prophylactic agent for pollakiuria or urinary incontinence. Especially, the compound may be used for therapy or prophylaxis of pollakiuria or urinary incontinence caused by diseases such as urinary urgency, neurogenic bladder, nocturia, overactive bladder, unstable bladder, pollakiuria nervosa, psychogenic pollakiuria, enuresis, cystospasm, chronic cystitis, chronic prostatitis, benign prostatic hypertrophy and prostate cancer. The term "neurogenic bladder" means that the function of urinary storage or voiding of the lower urinary tract is in an abnormal state because of some damage of the nerve governing the lower urinary tract comprising bladder, urethra and external urethral sphincter. Examples of the diseases which damage the nerve include cerebrovascular disease, brain tumor, brain injury, encephalitis, brain tumor, normal pressure hydrocephalus, dementia, Parkinson's disease, striatonigral degeneration, progressive supranuclear palsy, olivo-ponto-cerebellar atrophy, Shy-Drager syndrome, spinal cord injury, vascular disease of spinal cord, spinal cord tumor, myelitis, cervical cord compression disease, syringomyelia, multiple sclerosis, spina bifida, myelo-meningocele, Tethered cord syndrome and myelopathy. The compound may be preferably used as a therapeutic or prophylactic agent for pollakiuria or urinary incontinence caused by, inter alia, neurogenic bladder, overactive bladder, unstable bladder, chronic cystitis, chronic prostatitis or benign prostatic hypertrophy. However, use of the therapeutic or prophylactic agent for pollakiuria or urinary incontinence is not restricted to these diseases.

The pharmaceutical containing the compound is effective not only for human but also for mammals other than human, such as mouse, rat, hamster, rabbit, cat, dog, bovine, sheep and monkey.

The compound may be used not only as a therapeutic or prophylactic agent for pollakiuria or urinary incontinence as described above, but also in a method for treating or preventing pollakiuria or urinary incontinence, or in the production of a pharmaceutical for treating or preventing pollakiuria or urinary incontinence.

When clinically using the compound as a therapeutic or prophylactic agent for pollakiuria or urinary incontinence, the pharmaceutical may be the free base or an acid addition salt thereof alone, or the pharmaceutical may optionally be admixed with additives such as vehicles, stabilizers, preservatives, buffering agents, solubilizers, emulsifiers, diluents and isotonic agents. The administration form include formulations for oral administration such as tablets, capsules, granules, powders and syrups; formulations for parenteral administration such as injection solutions, suppositories and liquids; and formulations for topical administration such as ointments, creams and patches.

The therapeutic or prophylactic agent for pollakiuria or urinary incontinence preferably contains the above-described effective ingredient in an amount of 0.00001 to 90% by weight, more preferably 0.0001 to 70% by weight. Although the administration dose may be appropriately selected depending on the symptom, age, body weight, administration method and the like, the dose of the effective component per adult per day may be 0.1 µg to 1 g in the case of administration by injection, 1 µg to 10 g in the case of oral administration, and 1 µg to 10 g in the case of administration by a patch, and may be administered at one time or dividedly in several times.

The therapeutic or prophylactic agent for pollakiuria or urinary incontinence may also be used in combination with other therapeutic or prophylactic agents for urinary dysfunction, or with other therapeutic or prophylactic agents for diseases which cause urinary dysfunction.

Examples of the other therapeutic or prophylactic agents for urinary dysfunction include anticholinergic agents such as Propantheline, Oxybutynin, Propiverine, Tolterodine, Temiverine, Trospium, Darifenacin, Solifenacin and KRP-197; smooth muscle relaxants such as Flavoxate; potassium channel openers such as NS-8, ZD-0947, KW-7158, ABT-598 and WAY-151616; calcium channel antagonists such as Nifedipine and Flunarizine; skeletal muscle relaxants such as Baclofen, Diazepam and Lanperisone; antidepressants such as Imipramine, Desipramine, Fluoxetine, Fluvoxamine, Milnacipran, Paroxetine and Duloxetine; vasopressin agonists such as Desmopressin; tachykinin antagonists such as TAK-637, SR-48968, Talnetant and Aprepitant; β agonists such as Clenbuterol, KUC-7483, YM-178 and GW-427353; vanilloid agonists such as capsaicin and resiniferatoxin; vanilloid antagonists such as SB-705498, AMG-0347, BCTC, A-784168, SPM-955 and DD-161515; PGE antagonists such as ONO-8711 and ONO-8992; COX inhibitors such as Flurbiprofen; α1 agonists such as R-450; α1 antagonists such as Doxazosin, Indramin, Terazosin, Urapidil, Alfuzosin, Prazosin, Naftopidil, Tamsulosin, Selodosin, Fiduxosin and KMD-3213; and sodium channel blockers such as Vinpocetine, GW-286103, Zonisamide, Mexiletine, Ranolazine and Riluzole.

Examples of the diseases which cause urinary dysfunction include benign prostatic hypertrophy, prostate cancer, diabetes, cerebrovascular disease, dementia including Alzheimer's disease, depression, Parkinson's disease and multiple sclerosis. Examples of the therapeutic or prophylactic agent for benign prostatic hypertrophy include 5α-reductase inhibitors such as Finasteride, Dutasteride, Izonsteride, CS-891 and MK-434; androgen receptor antagonists such as Flutamide, Bicalutamide and Nilutamide; antiandrogen drugs such as Allylestrenol, Chlormadinone, Gestonorone, Cyproterone, Osaterone and Nomegestrol; endothelin antagonists such as SB-217242 and TA-0201; botanical drugs such as Eviprostat and Cernilton; and the above-described α1 antagonists.

Examples of the therapeutic or prophylactic agent for prostate cancer include LH-RH agonists such as Leuprorelin, Goserelin, Buserelin, Nafarelin and Triptorelin; LH-RH antagonists such as Cetrorelix, Ganirelix and Abarelix; the above-mentioned 5α-reductase inhibitors, the above-mentioned androgen receptor antagonists; and above-mentioned antiandrogen drugs.

Examples of the therapeutic or prophylactic agent for diabetes include anti-insulin resistance drugs such as Pioglitazone, Troglitazone and Rosiglitazone; insulin secretion enhancers such as Tolbutamide, Chlorpropamide, Tolazamide, Acetohezamide, Glyclopyramide, Glibenclamide, gliclazide, Glimepiride, Repaglinide and Nateglinide; biguanides such as Metformin and Buformin; α-glucosidase inhibitors such as insulin, Acarbose, Voglibose, Miglitol and Emiglitate; β3 adrenaline receptor agonists such as AJ-9677, SR-58611-A, SB-226552 and AZ40140; and other drugs such as Erogoset, Pramlintide, Leptin and BAY-27-9955.

Examples of the therapeutic or prophylactic agent for cerebrovascular disease include Aniracetam, Ibudilast, Tiapride, Cardiochrome, citicoline, γ-aminobutyric acid, ifenprodil, Nicergorine, vinpocetine, Nizofenone, bencyclane and cinepazide.

Examples of the therapeutic or prophylactic agent for dementia including Alzheimer's disease include Donepezil.

Examples of the therapeutic or prophylactic agent for depression include the above-mentioned antidepressants.

Examples of the therapeutic or prophylactic agent for Parkinson's disease include Amantadine, Trihexyphenidyl, Bromocriptine, Levodopa, Carbidopa and Apomorphine.

Examples of the therapeutic or prophylactic agent for multiple sclerosis include steroid drugs and interferon-β-1b.

EXAMPLES

Our benzylamine derivatives will now be described more concretely by way of examples thereof.

Reference Example 1

N-(5-((1R,2S)-2-Amino-1-hydroxypropyl)-2-hydroxyphenyl)methanesulfonamide (4)

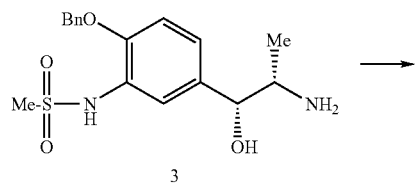

3

-continued

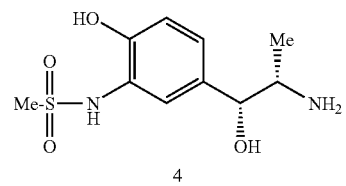

4

To a solution of the amine derivative (3) (195 mg, 0.556 mmol) synthesized according to the method described in Reference Example 1 of WO2005/040093 in methanol (6 mL) was added 10% palladium/carbon (60 mg) and the resulting mixture was stirred under a hydrogen atmosphere at room temperature for 2.5 hours. The reaction mixture was filtered and the filtrate was concentrated to obtain the desired amine (4) as a brown solid (153 mg). The desired amine (4) was used in the subsequent reaction without purification.

$^1$H NMR (400 MHz, CD$_3$OD) δ (ppm): 1.15 (d, J=6.8 Hz, 3H), 2.97 (s, 3H), 3.46 (m, 1H), 4.85 (d, J=3.4 Hz, 1H), 6.95 (d, J=8.3 Hz, 1H), 7.14 (dd, J=2.2, 8.3 Hz, 1H), 7.40 (d, J=2.2 Hz, 1H).

Example 1

N-(5-((1R,2S)-2-(3,5-Dimethoxybenzylamino)-1-hydroxypropyl)-2-hydroxyphenyl)methane-sulfonamide (5)

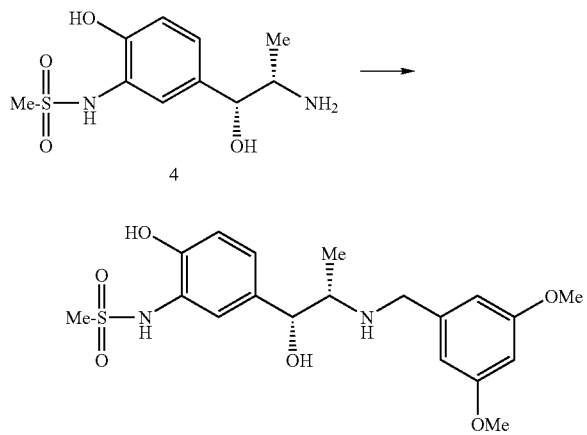

To a solution of the amine (4) (363 mg, 1.39 mmol) and 3,5-dimethoxybenzaldehyde (301 mg, 1.81 mmol) in methanol (10 mL) was added borane-pyridine complex (445 μL, 4.18 mmol) at 40° C. and the resulting mixture was stirred for 2 hours. The reaction mixture was cooled to room temperature and water was added thereto, followed by extraction with a mixed solvent (ethyl acetate:methanol=10:1) and subsequent washing of the organic layer with saturated brine. The organic layer was dried and concentrated and the obtained crude product was purified by amine silica gel column chromatography (eluent; chloroform:methanol=7:1) to obtain the desired amine (5) as a pale yellow solid (329 mg, Yield: 57%).

$^{1}$H NMR (400 MHz, CD$_{3}$OD) δ (ppm): 1.11 (d, J=6.4 Hz, 3H), 2.83 (m, 1H), 2.89 (s, 3H), 3.61 (d, J=13.2 Hz, 1H), 3.73 (d, J=13.2 Hz, 1H), 3.73 (s, 6H), 4.48 (d, J=6.0 Hz, 1H), 6.34 (t, J=2.4 Hz, 1H), 6.37 (d, J=2.4 Hz, 2H), 6.84 (d, J=8.0 Hz, 1H), 6.99 (dd, J=2.0, 8.0 Hz, 1H), 7.32 (d, J=2.0 Hz, 1H).

To the dioxane solution (1 mL) of the obtained amine (5) (47 mg, 0.11 mmol) was added 4N hydrochloric acid/dioxane solution (0.04 mL) and the resulting mixture was freeze-dried to obtain hydrochloric acid salt of the amine (5) as a white solid (27 mg, Yield: 55%).

$^{1}$H NMR (400 MHz, DMSO-d6) δ (ppm): 1.00 (d, J=6.8 Hz, 3H), 2.91 (s, 3H), 3.23 (m, 1H), 3.76 (s, 6H), 4.18 (m, 2H), 5.13 (br, 1H), 6.03 (d, J=3.6 Hz, 1H), 6.51 (t, J=2.4 Hz, 1H), 6.86 (d, J=2.4 Hz, 2H), 6.92 (d, J=8.0 Hz, 1H), 6.99 (dd, J=2.0, 8.0 Hz, 1H), 7.18 (d, J=2.0 Hz, 1H), 8.78 (s, 1H), 9.10 (br, 1H), 9.19 (br, 1H), 10.00 (s, 1H).

Example 2

N-(5-((1R,2S)-2-(3,5-Bis(trifluoromethyl)benzylamino)-1-hydroxypropyl)-2-hydroxyphenyl)methanesulfonamide (6)

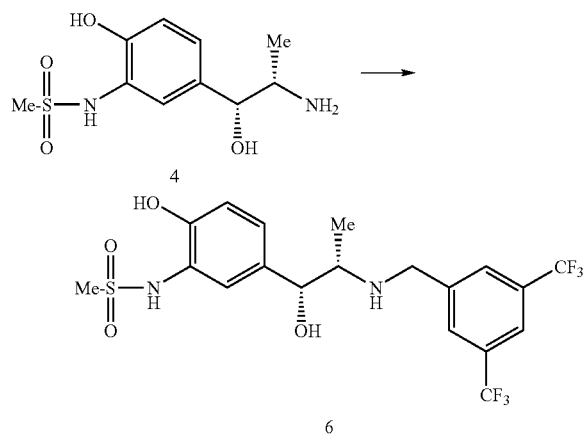

To a solution of the amine (4) (107 mg, 0.41 mmol) and 3,5-bis(trifluoromethyl)benzaldehyde (90 μL, 0.54 mmol) in methanol (4 mL) was added borane-pyridine complex (130 μL, 1.24 mmol) at 40° C. and the resulting mixture was stirred for 1.5 hours. The reaction mixture was cooled to room temperature and water was added thereto, followed by extraction with a mixed solvent (ethyl acetate:methanol=10:1) and subsequent washing of the organic layer with saturated brine. The organic layer was dried and concentrated and the obtained crude product was purified by amine silica gel column chromatography (eluent; chloroform:methanol=7:1) to obtain the desired amine (6) as a white solid (132 mg, Yield: 66%).

$^{1}$H NMR (400 MHz, CD$_{3}$OD) δ (ppm): 1.07 (d, J=6.4 Hz, 3H), 2.80 (m, 1H), 2.90 (s, 3H), 3.87 (d, J=14.0 Hz, 1H), 3.95 (d, J=14.0 Hz, 1H), 4.55 (d, J=5.6 Hz, 1H), 6.85 (d, J=8.4 Hz, 1H), 7.02 (dd, J=2.0, 8.0 Hz, 1H), 7.34 (d, J=2.0 Hz, 1H), 7.81 (brs, 1H), 7.89 (brs, 2H).

Example 3

N-(5-((1R,2S)-2-(3,5-Dichlorobenzylamino)-1-hydroxypropyl)-2-hydroxyphenyl)methane-sulfonamide (7)

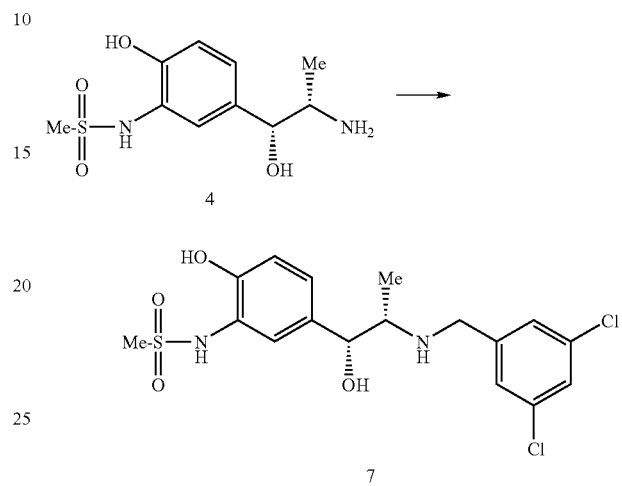

To a solution of the amine (4) (105 mg, 0.40 mmol) and 3,5-dichlorobenzaldehyde (95 mg, 0.52 mmol) in methanol (4 mL) was added borane-pyridine complex (130 μL, 1.21 mmol) at 40° C. and the resulting mixture was stirred for 1.5 hours. The reaction mixture was cooled to room temperature and water was added thereto, followed by extraction with a mixed solvent (ethyl acetate:methanol=10:1) and subsequent washing of the organic layer with saturated brine. The organic layer was dried and concentrated and the obtained crude product was purified by amine silica gel column chromatography (eluent; chloroform:methanol=7:1) to obtain the desired amine (7) as a white solid (76 mg, Yield: 45%).

$^{1}$H NMR (400 MHz, CD$_{3}$OD) δ (ppm): 1.07 (d, J=6.4 Hz, 3H), 2.76 (m, 1H), 2.91 (s, 3H), 3.67 (d, J=14.0 Hz, 1H), 3.76 (d, J=14.0 Hz, 1H), 4.48 (d, J=5.6 Hz, 1H), 6.86 (d, J=8.4 Hz, 1H), 7.01 (dd, J=2.0, 8.4 Hz, 1H), 7.20 (d, J=2.0 Hz, 2H), 7.29 (t, J=2.0 Hz, 1H), 7.32 (d, J=2.0 Hz, 1H).

Example 4

N-(2-Hydroxy-5-((1R,2S)-1-hydroxy-2-(3,4,5-trimethoxybenzylamino)propyl)phenyl)methane-sulfonamide (8)

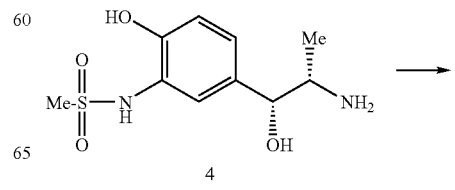

-continued

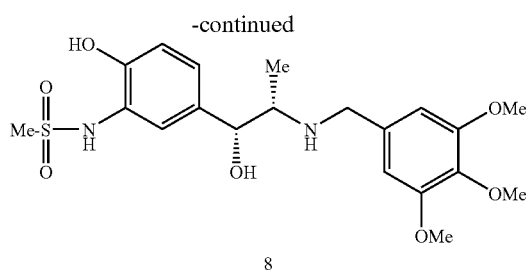

8

To a solution of the amine (4) (111 mg, 0.43 mmol) and 3,4,5-trimethoxybenzaldehyde (111 mg, 0.55 mmol) in methanol (4 mL) was added borane-pyridine complex (135 μL, 1.28 mmol) at 40° C. and the resulting mixture was stirred for 1.5 hours. The reaction mixture was cooled to room temperature and water was added thereto, followed by extraction with a mixed solvent (ethyl acetate:methanol=10:1) and subsequent washing of the organic layer with saturated brine. The organic layer was dried and concentrated and the obtained crude product was purified by amine silica gel column chromatography (eluent; chloroform:methanol=7:1) to obtain the desired amine (8) as a white solid (67 mg, Yield: 36%).

$^1$H NMR (400 MHz, CD$_3$OD) δ (ppm): 1.12 (d, J=6.4 Hz, 3H), 2.82 (m, 1H), 2.89 (s, 3H), 3.61 (d, J=12.8 Hz, 1H), 3.72 (s, 3H), 3.73 (d, J=12.8 Hz, 1H), 3.80 (s, 6H), 4.46, (d, J=6.4 Hz, 1H), 6.52 (s, 2H), 6.84 (d, J=8.4 Hz, 1H), 6.99 (dd, J=2.0, 8.4 Hz, 1H), 7.32 (d, J=2.0 Hz, 1H).

Example 5

N-(5-((1R,2S)-2-(3,5-Dimethylbenzylamino)-1-hydroxypropyl)-2-hydroxyphenyl)methane-sulfonamide (9)

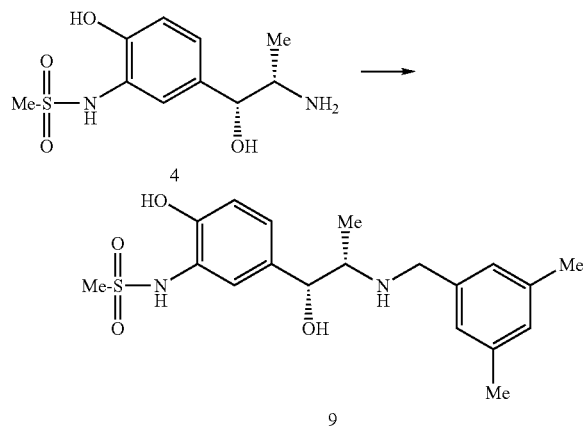

To a solution of the amine (4) (131 mg, 0.50 mmol) and 3,5-dimethylbenzaldehyde (90 μL, 0.65 mmol) in methanol (5 mL) was added borane-pyridine complex (160 μL, 1.50 mmol) at 40° C. and the resulting mixture was stirred for 1.5 hours. The reaction mixture was cooled to room temperature and water was added thereto, followed by extraction with a mixed solvent (ethyl acetate:methanol=10:1) and subsequent washing of the organic layer with saturated brine. The organic layer was dried and concentrated and the obtained crude product was purified by amine silica gel column chromatography (eluent; chloroform:methanol=7:1) to obtain the desired amine (9) as a white solid (62 mg, Yield: 33%).

$^1$H NMR (400 MHz, CD$_3$OD) δ (ppm): 1.10 (d, J=6.4 Hz, 3H), 2.25 (s, 6H), 2.82 (m, 1H), 2.88 (s, 3H), 3.60 (d, J=12.8 Hz, 1H), 3.73 (d, J=12.8 Hz, 1H), 4.49 (d, J=6.0 Hz, 1H), 6.79 (brs, 2H), 6.84 (d, J=8.4 Hz, 1H), 6.87 (brs, 1H), 6.98 (dd, J=2.0, 8.4 Hz, 1H), 7.31 (d, J=2.0 Hz, 1H).

Example 6

N-(5-((1R,2S)-2-(3,5-Diethoxybenzylamino)-1-hydroxypropyl)-2-hydroxyphenyl)methane-sulfonamide (10)

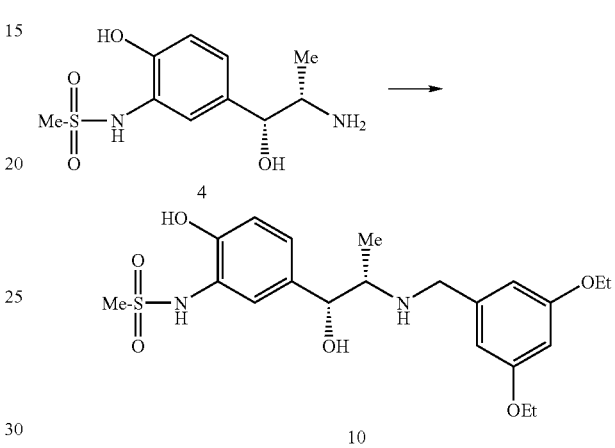

To a solution of the amine (4) (127 mg, 0.486 mmol) and 3,5-diethoxybenzaldehyde (123 mg, 0.632 mmol) in methanol (3.3 mL) was added borane-pyridine complex (155 μL, 1.46 mmol) at 40° C. and the resulting mixture was stirred for 2.5 hours. The reaction mixture was cooled to room temperature and water was added thereto, followed by extraction with a mixed solvent (ethyl acetate:methanol=10:1) and subsequent washing of the organic layer with saturated brine. The organic layer was dried and concentrated and the obtained crude product was purified by amine silica gel column chromatography (eluent; chloroform:methanol=7:1) to obtain the desired amine (10) as a yellow solid (114 mg, Yield: 54%).

$^1$H NMR (400 MHz, CD$_3$OD) δ (ppm): 1.14 (d, J=6.4 Hz, 3H), 1.39 (t, J=7.1 Hz, 6H), 2.88 (m, 1H), 2.93 (s, 3H), 3.63 (d, J=12.9 Hz, 1H), 3.76 (d, J=12.9 Hz, 1H), 3.99 (q, J=7.1 Hz, 4H), 4.52 (d, J=5.9 Hz, 1H), 6.35 (t, J=2.0 Hz, 1H), 6.38 (d, J=2.0 Hz, 2H), 6.88 (d, J=8.3 Hz, 1H), 7.02 (dd, J=2.0, 8.3 Hz, 1H), 7.36 (d, J=2.0 Hz, 1H).

Example 7

Relaxing Activity Test Against Isolated Bladder Smooth Muscle in Rat

This method was carried out in accordance with the literature [J. Pharmacol. Exp. Ther., 293, 939 (2000)]. Each bladder was isolated from a normal Spague-Dawley rat, and a bladder section of the size of about 2×10 mm was prepared in the nutrient solution (Krebs solution [NaCl 118 mM; KCl 4.7 mM; NaH$_2$PO$_4$ 1.1 mM; glucose 10 mM; NaHCO$_3$ 25 mM; MgCl$_2$.7H$_2$O 1 mM; CaCl$_2$.2H$_2$O 2.5 mM]) sufficiently oxygenated with 95% O$_2$+5% CO$_2$. The sample was suspended in a Magnus tube filled with the nutrient solution (Krebs solution) aerated with 95% O$_2$+5% CO$_2$ at 37° C., and stabilized under a load of 0.5 g for 60 minutes or longer. The resting tension of the bladder sample was recorded in a pen recorder through a tension transducer. The test compound was cumulatively applied about every 10 minutes. The pharmacological effect was evaluated by taking the relaxation response due to addition of 10 μM forskolin as 100%, and the logarithm of the concentration of the test compound, when the 50% relaxation was achieved, was expressed as pEC50. The test compound was dissolved in distilled water or aqueous 10% dimethylsulfoxide solution.

As a result, the compounds showed the relaxing activity against the resting tension of isolated bladder smooth muscle in rat, and their pEC50s were 6.64-7.44 as shown in Table 2.

TABLE 2

| Compound | pEC50 |
| --- | --- |
| Compound of Example 1 | 6.64 |
| Compound of Example 2 | 7.44 |
| Compound of Example 3 | 7.05 |
| Compound of Example 4 | 7.13 |
| Compound of Example 5 | 6.82 |

Example 8

Measurement of Number of Voiding Episodes in Rat Natural Voiding Behavior Test

This method was carried out according to the literature [Jpn. J. Pharmacol., 87, 27 (2001)]. Each female Spague-Dawley rat was placed in a urine collection cage, and an electronic balance was placed under the cage. Excreted urine was allowed to fall into a urine collection tray placed on the electronic balance, and its change in weight every 10 seconds was scaled with time through a personal computer. Not less than 0.1 g of the change in weight was regarded as indicative of urination, and the weight of 1 g was regarded as corresponding to 1 mL of urine. Drug administration was carried out subcutaneously, and the number of voiding episodes was measured for 1 hour before and after the drug administration, to observe its change (number of cases: 11 to 18/group).

As a result, as shown in Table 3, the compounds showed a significant and remarkable effect of decreasing the frequency of voiding episodes compared to that before the drug administration, so that the compounds were confirmed to have an anti-pollakiuria activity.

The compound 1 described in Japanese Translated PCT Patent Application Laid-open No. 2002-512639, which is a β3 agonist, also showed a dose-dependent and significant effect of decreasing the frequency of voiding episodes. On the other hand, the compound 11 which is being developed as a β3 agonist therapeutic agent for pollakiuria did not show a significant effect, at a dose of 3 mg/kg, of decreasing the frequency of voiding episodes in comparison with the vehicle-treated group, and a significant effect of decreasing the frequency of voiding episodes was observed only at 3 hours after the administration.

Among the β3 agonists used for comparison, the compound 1 was synthesized according to the method described in JP 7-206806 A. The compound 11 was synthesized according to the method described in WO 99/20607.

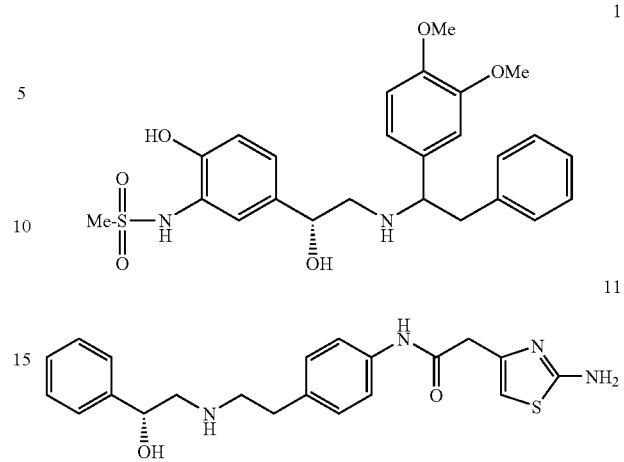

Significant difference test was carried out by student's-test or williams test, wherein a significance level of less than 5% was accepted as significant (* in the table).

TABLE 3

| Compound | Dose | Number of Voiding Episodes |
| --- | --- | --- |
| Compound of Example 1 | Vehicle | 1.37 ± 0.17 |
| | 0.1 mg/kg | 1.06 ± 0.17 |
| | 0.3 mg/kg | 0.83 ± 0.12* |
| | 1 mg/kg | 0.94 ± 0.17* |
| Compound of Example 2 | Vehicle | 1.25 ± 0.30 |
| | 3 mg/kg | 0.45 ± 0.21* |
| Compound of Example 3 | Vehicle | 1.25 ± 0.30 |
| | 3 mg/kg | 0.50 ± 0.15* |
| Compound of Example 4 | Vehicle | 1.33 ± 0.26 |
| | 3 mg/kg | 0.33 ± 0.19* |
| Compound of Example 5 | Vehicle | 1.25 ± 0.30 |
| | 3 mg/kg | 0.50 ± 0.15* |
| Compound 1 | Vehicle | 1.58 ± 0.23 |
| | 0.03 mg/kg | 1.17 ± 0.21 |
| | 0.1 mg/kg | 1.00 ± 0.17* |
| | 0.3 mg/kg | 0.58 ± 0.15* |
| Compound 11 | Vehicle | 0.75 ± 0.18 |
| | 3 mg/kg | 0.67 ± 0.19 |

Example 9

Evaluation of Effect on Cardiovascular System in Anesthetized Rats

This method was carried out in accordance with the literature [Experimental Methods in Pharmacology, 5th Revised Edition, p. 168, KYODO ISHO SHUPPAN CO., LTD.]

Each female Spague-Dawley rat was anesthetized with urethane, and a polyethylene cannula was inserted into the left common carotid artery and fixed therein, to measure the mean blood pressure and the heart rate. After confirming that the blood pressure became stable, the drug was administered cumulatively and subcutaneously, and changes in the mean blood pressure and the heart rate were observed for 30 minutes following the administration of each dose of the test drug. Data were represented as amounts of the changes (blood pressure: mmHg, heart rate: %) relative to values before the administration (number of cases: 3 to 8/group).

As a result, as shown in Table 4, the compound did not show a significant change, at a dose of 0.3 (the pharmacologically effective dose) to 3 mg/kg (10 times as much as the pharmacologically effective dose), in the blood pressure and the heart rate in comparison with the vehicle-treated group. On the other hand, the compound 1 showed a significant effect, at a dose of 0.3 mg/kg (3 times as much as the pharmacologically effective dose), of increasing the heart rate in comparison with the vehicle-treated group, and showed a significant effect, at a dose of 1 mg/kg (10 times as much as the pharmacologically effective dose), of decreasing the blood pressure. The compound 11 also showed a significant effect, at a dose of 3 mg/kg, of increasing the heart rate in comparison with the vehicle-treated group. Significant difference test was performed using student's-test or williams test, wherein a significance level of less than 5% was accepted as significant (* in the table).

TABLE 4

| Compound | Dose | Change in Blood Pressure (mmHg) | Change in Heart Rate (%) |
|---|---|---|---|
| Compound of Example 1 | Vehicle | −25.7 ± 3.1 | 115.2 ± 3.4 |
| | 0.3 mg/kg | −25.2 ± 4.7 | 121.7 ± 4.2 |
| | 1 mg/kg | −25.4 ± 2.3 | 126.4 ± 5.1 |
| | 3 mg/kg | −25.0 ± 3.6 | 135.2 ± 8.4 |
| Compound 1 | Vehicle | −14.2 ± 3.0 | 104.7 ± 0.8 |
| | 0.3 mg/kg | −22.2 ± 3.0 | 120.0 ± 3.8* |
| | 1 mg/kg | −25.8 ± 3.5* | 139.0 ± 4.1* |
| Compound 11 | Vehicle | −14.6 ± 2.5 | 106.3 ± 1.5 |
| | 3 mg/kg | −17.1 ± 3.5 | 133.5 ± 8.2* |

Example 10

Evaluation of Effect on Cardiovascular System in Conscious Rats

This method was carried out in accordance with the literature [Experimental Methods in Pharmacology, 5th Revised Edition, p. 168, KYODO ISHO SHUPPAN CO., LTD.]

Each female Spague-Dawley rat was anesthetized with ether, and a polyethylene cannula was inserted into the left common carotid artery and fixed therein, followed by subcutaneously indwelling a cannula for drug administration. After recovery from anesthesia, the mean blood pressure and the heart rate were measured under free moving conditions. After confirming that the blood pressure became stable, the drug was administered subcutaneously, and changes in the mean blood pressure and the heart rate were observed. Changes relative to values before the administration were observed for 30 minutes following the administration of each dose of the test drug, and comparisons were made with the vehicle-treated group (change in the blood pressure: mmHg, change in the heart rate: %) (number of cases: 4 to 5/group).

As a result, as shown in Table 5, the compound did not show a significant change, at a dose of 0.3 mg/kg (the pharmacologically effective dose), in the blood pressure and the heart rate in comparison with the vehicle-treated group. On the other hand, the compound 1 showed significant effects, at a dose of 0.1 mg/kg (the pharmacologically effective dose), of decreasing the blood pressure and increasing the heart rate in comparison with the vehicle-treated group. The compound 11 also showed a significant effect, at a dose of 3 mg/kg, of increasing the heart rate in comparison with the vehicle-treated group. Significant difference test was performed using student's t-test, wherein a significance level of less than 5% was accepted as significant (* in the table).

In Examples 9 and 10, it was shown that the compound has much less possibility of occurrence of side effects on cardiovascular system than existing β3 agonists.

TABLE 5

| Compound | Dose | Change in Blood Pressure (mmHg) | Change in Heart Rate (%) |
|---|---|---|---|
| Compound of Example 1 | Vehicle | −0.5 ± 2.3 | 103.9 ± 1.0 |
| | 0.3 mg/kg | −6.5 ± 5.5 | 107.7 ± 3.5 |
| Compound 1 | Vehicle | 7.8 ± 5.3 | 100.1 ± 2.5 |
| | 0.1 mg/kg | −29.5 ± 6.8* | 114.5 ± 3.9* |
| Compound 11 | Vehicle | −8.3 ± 2.5 | 100.2 ± 1.3 |
| | 3 mg/kg | −22.5 ± 5.6 | 114.5 ± 3.1* |

Example 11

Evaluation of Agonistic Activity Against Human Adrenergic β Receptors

This method was carried out according to the literature [J. Pharmacol. Exp. Ther., 271, 1253 (1994)] or [Naunyn-Schmiedeberg's Arch. Pharmacol., 369, 151 (2004)], using the amount of the production of cAMP as an index. The agonistic activity against human adrenergic β3 receptor was evaluated using SK-N-MC cells in the presence of a selective adrenergic β1 receptor antagonist (CGP-20712A, 1 μM). Evaluation of the agonistic activities against human adrenergic β2 and β1 receptors was carried out using CHO-K1 cells forcibly-expressed each receptor. Their cells were cultured in a culture flask. In assay day, they were detached and collected with EDTA, followed by dispensing in a 384-well plate so as to attain 10,000 cells/well. The test compound of each concentration was added to each well and allowed to react in a $CO_2$ incubator at 37° C. for 30 minutes, followed by quantification of the produced cAMP using cAMP detection kit (Perkinelmer). The logarithm of the 50% reaction concentration of each test compound was calculated taking the reaction by 100 or 300 nM Isoproterenol as 100%. The test drug was added up to 10 μM, and in cases where reaction of not less than 50% was not observed at this concentration, the result was represented as n.d. (not detected).

As a result, the compounds were shown to have the agonistic activity against human adrenergic β3 receptor.

Further, all the compounds were considered to be excellent in the selectivity on β3 receptor and have similar properties.

TABLE 6

| Compound | β3 | β2 | β1 |
|---|---|---|---|
| Compound of Example 1 | 7.40 | 5.63 | n.d. |
| Compound of Example 2 | 7.50 | n.d. | n.d. |
| Compound of Example 3 | 7.66 | 5.97 | n.d. |
| Compound of Example 4 | 7.48 | n.d. | n.d. |
| Compound of Example 5 | 7.14 | n.d. | n.d. | nd.: not detected at 10 μM

Example 12

Relaxing Activity Against Isolated Bladder Smooth Muscle in Human

This method was carried out in accordance with the literature [J. Urology, 165, 240 (2001)].

A normal part (non-cancerous part) of the bladder removed from a human male (32-72 years old) by bladder cancer surgery was used. A bladder section sizing about 3×10 mm was prepared in the nutrient solution (Krebs solution [NaCl 118 mM; KCl 4.7 mM; $NaH_2PO_4$ 1.2 mM; glucose 10 mM; $NaHCO_3$ 25 mM; $MgCl_2.7H_2O$ 1.2 mM; $CaCl_2.2H_2O$ 2.5 mM]) sufficiently oxygenated with 95% $O_2$+5% $CO_2$. The sample was suspended in a Magnus tube filled with the nutrient solution (Krebs solution) aerated with 95% $O_2$+5% $CO_2$ at 37° C., and stabilized under a load of 0.5 g for 60 minutes or longer. The resting tension of the bladder sample was recorded in a pen recorder through a tension transducer. The test compound was cumulatively applied about every 10 minutes. The test compound was dissolved in distilled water or aqueous 10% DMSO solution (number of cases: 3 to 4/group).

As a result, as shown in Table 7, the compounds showed the relaxing activity, on the isolated sample, of not less than 70% at the concentration of 10 μM, taking the relaxation response by addition of 10 μM forskolin as 100%. Their pEC50s were 6.15-6.25, and they were confirmed to show a strong effect also in human, as well.

TABLE 7

| Compound | pEC50 |
|---|---|
| Compound of Example 1 | 6.25 |
| Compound of Example 4 | 6.15 |
| Compound of Example 5 | 6.24 |

Industrial Applicability

The novel benzylamine derivatives or pharmaceutically acceptable acid addition salts thereof may be used as a pharmaceutical, especially a therapeutic or prophylactic agent for pollakiuria or urinary incontinence, containing the derivative as an effective component.

The invention claimed is:

1. A benzylamine derivative represented by General Formula (I)

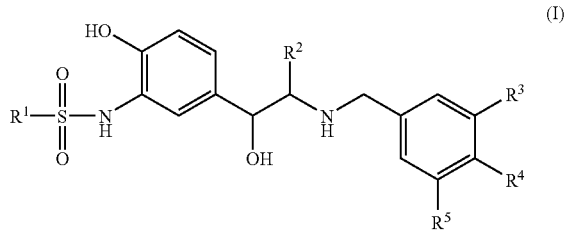

(wherein $R^1$ is $C_1$-$C_6$ alkyl; $R^2$ is $C_1$-$C_6$ alkyl; $R^3$ and $R^5$ are each independently $C_1$-$C_6$ alkyl, $C_1$-$C_6$ haloalkyl, $C_1$-$C_6$ alkoxy or halogen; and $R^4$ is hydrogen or $C_1$-$C_6$ alkoxy) or a pharmaceutically acceptable acid addition salt thereof.

2. The benzylamine derivative or the pharmaceutically acceptable acid addition salt thereof according to claim 1, wherein:
$R^1$ is methyl, ethyl, propyl, isopropyl or tert-butyl; and
$R^2$ is methyl, ethyl, propyl or isopropyl.

3. The benzylamine derivative or the pharmaceutically acceptable acid addition salt thereof according to claim 1, wherein:
$R^3$ and $R^5$ are each independently methyl, ethyl, fluoromethyl, difluoromethyl, trifluoromethyl, methoxy, ethoxy or chloro; and
$R^4$ is hydrogen, methoxy, ethoxy, propoxy or isopropoxy.

4. The benzylamine derivative or the pharmaceutically acceptable acid addition salt thereof according to claim 1, wherein:
$R^2$ is methyl;
$R^3$ and $R^5$ are each independently methyl, ethyl, fluoromethyl, difluoromethyl, trifluoromethyl, methoxy, ethoxy or chloro; and
$R^4$ is hydrogen, methoxy, ethoxy, propoxy or isopropoxy.

5. The benzylamine derivative or the pharmaceutically acceptable acid addition salt thereof according to claim 1, wherein:
$R^1$ and $R^2$ are methyl;
$R^3$ and $R^5$ are each independently methyl, trifluoromethyl, methoxy or chloro; and
$R^4$ is hydrogen or methoxy.

6. The benzylamine derivative or the pharmaceutically acceptable acid addition salt thereof according to claim 1, wherein:
$R^1$ and $R^2$ are methyl;
$R^3$ and $R^5$ are simultaneously methyl, trifluoromethyl, methoxy or chloro; and
$R^4$ is hydrogen.

7. A pharmaceutical comprising the benzylamine derivative or the pharmaceutically acceptable acid addition salt thereof according to claim 1.

8. A therapeutic agent for pollakiuria or urinary incontinence, comprising said benzylamine derivative or the pharmaceutically acceptable acid addition salt thereof according to claim 1.

9. A method of treating of pollakiuria or urinary incontinence, comprising administering an effective amount of said benzylamine derivative or the pharmaceutically acceptable acid addition salt thereof according to claim 1.

10. A pharmaceutical compound for treating pollakiuria or urinary incontinence comprising the benzylamine derivative or the pharmaceutically acceptable acid addition salt thereof according to claim 1 and at least one other therapeutic agent for urinary dysfunction or diseases that cause urinary dysfunction.

11. The benzylamine derivative or the pharmaceutically acceptable acid addition salt thereof according to claim 1, that treats pollakiuria or urinary incontinence.

* * * * *